United States Patent [19]

Hostetler et al.

[11] Patent Number: 4,692,433

[45] Date of Patent: Sep. 8, 1987

[54] METHOD AND COMPOSITION FOR REGULATING SERUM CALCIUM LEVELS OF MAMMALS

[75] Inventors: Karl Y. Hostetler; Leonard J. Deftos, both of Del Mar, Calif.

[73] Assignee: The Regents of the University of California, Berkeley, Calif.

[21] Appl. No.: 761,751

[22] Filed: Aug. 1, 1985

Related U.S. Application Data

[63] Continuation-in-part of Ser. No. 541,125, Oct. 12, 1983, abandoned.

[51] Int. Cl.$^4$ .................. A61K 31/245; A61K 9/42; A61K 37/30; A61K 37/24
[52] U.S. Cl. ........................... 514/12; 514/808; 514/159; 424/450
[58] Field of Search ............. 514/808, 12; 424/38

[56] References Cited

U.S. PATENT DOCUMENTS

| | | | |
|---|---|---|---|
| 4,151,276 | 4/1979 | Caulen et al. | 424/111 |
| 4,241,051 | 12/1980 | Christie et al. | 424/177 |
| 4,342,826 | 8/1982 | Cole | 435/188 |
| 4,459,295 | 7/1984 | Higuchi et al. | 424/230 |

OTHER PUBLICATIONS

Taylor et al, cited in Chem. Abstracts, vol. 93:184604z.
Epand et al., cited in Chem. Abstracts, vol. 99:152321n.
Potts et al, cited in Chem. Abstracts, vol. 72:51369w.
Hemker et al, The Lancet, 1-12-80, pp. 70-71.

*Primary Examiner*—Johnnie R. Brown
*Assistant Examiner*—Jacqueline M. Stone
*Attorney, Agent, or Firm*—Poms, Smith, Lande & Rose

[57] ABSTRACT

Method for regulating serum calcium levels in mammals by orally administering a composition which includes a polypeptide hormone such as parathyroid hormone (PTH) or calcitonin. The polypeptide hormone is protected from destruction in the digestive tract by encapsulation in liposomes. The liposome preferably includes a cationic amphiphilic agent so that the surface of the liposome has a net positive charge. Agents for enhancing the action of the liposome encapsulated hormones are also disclosed.

22 Claims, No Drawings

METHOD AND COMPOSITION FOR REGULATING SERUM CALCIUM LEVELS OF MAMMALS

This invention was made with Government support under Grant No. AM 15888 awarded by the Department of Health and Human Services. The Government has certain rights in this invention.

This application is a Continuation-In-Part of Application Ser. No. 541,125 filed on Oct. 12, 1983, now abandoned, which is incorporated by this reference.

BACKGROUND OF THE INVENTION

Calcium is the most abundant and one of the most important minerals in the human body. Calcium is also an important cation in a wide variety of biological functions such as clotting of blood, the maintenance of normal heart beat and the initiation of neuromuscular and metabolic activities. The skeletal system provides an important reservoir for blood calcium in these processes. More than 99 percent of the calcium in the body is present in the skeleton as hydroxyapatite. Various diseases and metabolic disorders can cause the level of serum calcium to increase or decrease and thus cause serious biochemical and clinical abnormalities.

Of the factors which control calcium and skeletal metabolism, two polypeptide hormones, parathyroid hormone and calcitonin, are considered to be the most important. Parathyroid hormone (PTH) is an 84-amino acid peptide that acts to raise blood calcium and increase bone resorption. Calcitonin is a 32-amino acid polypeptide that acts to decrease bone resorption and lower blood calcium. Calcitonin is produced in the thyroid gland and perhaps at extra thyroidal sites and parathyroid hormone is produced in the parathyroid glands. The half life of calcitonin and of parathyroid hormone in the human body can be measured in minutes.

In general, the secretion of parathyroid hormone and calcitonin in the human body maintain normal mineral and skeletal metabolism. However, there are various disorders in which the production of these two peptides is deficient. Furthermore, there are diseases in which the administration of these two peptides alone or in combination to regulate blood calcium levels may be therapeutically important. Such diseases include but are not restricted to hypoparathyroidism, renal osteodystrophy, Paget's disease, malignancy with hypercalcemia and osteoporosis.

In order to treat and control the elevated or subnormal blood calcium levels due to abnormal calcium and skeletal metabolism, it has generally been the practice to treat individuals with either parathyroid hormone or calcitonin by injection using a syringe and needle. Furthermore, due to the relatively short half life of parathyroid hormone and calcitonin in the human body, it is necessary to continually administer the hormone by injection. Such a continuous schedule of hormone injections is burdensome, inconvenient and painful.

One way to improve the administration of these peptides is to increase the half life of the PTH and calcitonin which is injected into the individual. In our copending patent application Ser. No. 06/449,053, we disclose a method for increasing the time effectiveness of injected calcitonin by incorporating the calcitonin into liposomes prior to injection into the body.

Liposomes, which are also known as lipid vesicles, are composed of a spherical phospholipid bilayer enclosing an aqueous compartment. Due to the semipermeable nature of the lipid bilayer, the liposomes have been found useful as carriers for various biologically active agents since the lipid bilayer protects the entrapped agent from unwanted metabolic conversions. The use of liposome encapsulated calcitonin has been found effective in increasing the half life of calcitonin injections in the body to thereby decrease the frequency of injections required to produce and maintain the hypocalcemic effect of the hormone.

It would be desirable to provide PTH and calcitonin preparations which can be administered orally to the patient. In the past, attempts have been made to administer PTH and calcitonin by mouth. However, these methods have not resulted in orally effective preparations. Accordingly, it would be desirable to provide PTH and calcitonin preparations which produce their biological effect when taken orally.

SUMMARY OF THE INVENTION

In accordance with the present invention a method and composition are provided for regulating and controlling calcium and skeletal metabolism by the oral administration of the polypeptide hormones, calcitonin parathyroid hormone. The present invention is based upon the discovery that parathyroid hormone and calcitonin, which are encapsulated in phospholipid liposomes, can be taken orally to achieve their biological effect. It appears that the liposome protects the polypeptide hormone from destruction by digestive enzymes present in the small bowel and facilitates absorption of the polypeptide hormones.

As one feature of the present invention, the liposome or vesicle may include a sufficient amount of an amphiphilic agent to provide the surface of the liposome with a net positive charge in order to optimize the oral effectiveness of the preparations.

As another feature of the present invention, it was found that certain additives were effective in improving the action of liposome encapsulated polypeptide hormones when orally administered. These enhancement agents include aspirin derivatives such as sodium salicylate, sodium salicylamide acetylysalicylate, methylsalicylate, and the enzyme inhibitor aprotonin.

Although the exact mechanism by which the liposomes protect the polypeptide hormones from destruction in the small intestine is not known, it is believed that the liposome wall (lipid bilayer) protects the polypeptide hormone from destruction by digestive enzymes present in the small bowel and facilitate its absorption into the blood. The liposome entrapped calcitonin and parathyroid hormones in accordance with the present invention have been shown to affect the serum calcium levels in animals while the free hormone administered orally has no effect. The present invention therefore provides a new and unique method for regulating blood calcium levels by oral administration of liposomes containing either calcitonin or parathyroid hormone.

The above described and other features and attendant advantages of the present invention will become apparent as the invention becomes better understood by reference to the following detailed description.

DETAILED DESCRIPTION OF THE INVENTION

The present invention involves entrapping polypeptide hormones such as parathyoid hormone (PTH) and calcitonin in phospholipid liposomes so that the polypeptide hormone may be introduced orally (including nasal administration) into animals without being destroyed in the digestive tract. The present invention is useful in treating any number of diseases related to abnormal skeletal metabolism such as, but not limited to, hypercalcemia, Paget's diseases, renal osteodystrophy, and osteopososis.

Any of the well known procedures and techniques for preparing liposomes may be utilized in accordance with the present invention so long as encapsulation of the polypeptide hormone is provided. Basically, these procedures generally involve the production of a thin phospholipid film followed by agitation with an aqueous, buffered solution containing the hormones to give a dispersion of closed vesicles.

The polypeptide hormone is incorporated into the liposome as follows: the phospholipid components are dissolved in an organic solvent such as chloroform. The solvent is then removed to produce a lipid film. A buffer solution containing the polypeptide hormone is then added and mixed to form a suspension of the phospholipid film and polypeptide hormone. The suspension is then sonicated to form the liposome-entrapped polypeptide hormone. The suspension is then centrifuged at 120,000 times g for 16 hours to obtain a pellet consisting of liposome-entrapped hormone while the supernatant contains the unentrapped hormone. The liposomes in the pellet are then taken up in a small amount of buffer and subsequently used to influence calcium homestasis by oral administration.

The liposomes used in the present invention may be prepared from natural or synthetic phospholipids such as, but not limited to, phosphatidylcholine isolated from egg yolk, dimyristoylphosphatidylcholine and dipalmitoylphosphatidylcholine.

In addition to the phospholipid component of the liposome, a sufficient amount of an amphiphilic agent is preferably included to provide the surface of the liposome with a net positive charge. It has been determined that the net positive charge on the liposome surface enhances the oral effectiveness of the preparation. Suitable amphiphiles which can be used include alkyl amines having the general formula $C_nH_{2n+1}NH_2$ where n is 12 to 20. Stearylamine is preferred alkyl amine. The amount of amphiphile added should be sufficient to provide a net positive charge on the liposome surface. The molar percentage of alkylamine may vary widely from 0.5% up to about 99.5%. The preferred molar percentage of alkylamine is between about 1% and 20%.

Calcitonin of both natural and synthetic origin may be used for incorporation into the liposomes. Calcitonin is readily available polypeptide hormone which can be obtained from any number of suitable commercial outlets such as Peninsula Laboratories, San Carlos, CA. Calcitonin is a polypeptide hormone secreted by the parafollicular cells of the thyroid gland in mammals and by the ultimobranchial gland of birds and fish. Calcitonin includes 32 amino acids with a seven membered disulfide ring at the amino terminal end and a proline amide at the carboxy terminal end. The amino acid structure of the different species of calcitonin differ. All of the calcitonin species may be used in accordance with the present invention including bovine, porcine, ovine, salmon, eel, rat, and human. Human, salmon, and eel forms of the hormone are preferred because of their origin and biological potency. In addition, derivatives of each species of calcitonin such as aminosuberic substituted forms and other derivatives not occurring in nature are also of interest for use in the present application.

Calcitonin-salmon is of salmon origin or synthetic origin with both forms having 32 amino acids arranged in the same linear sequence. Salmon calcitonin appears to have actions essentially identical to calcitonins of mammalian origin, but with greater potency and longer duration of action. Any of the calcitonins which have been shown to be effective when administered by injection will also be effective when encapsulated and administered orally in accordance with our invention.

Parathyroid hormone is also available from commercial outlets such as Peninsula Laboratories, San Carlos, CA. Parathyroid hormone having the 1-34 amino acid fragment is preferred. Parathyroid hormone is a peptide with 84 amino acids. The amino acid sequence is different among the human, bovine and murine forms of the peptide. Although all species of parathyroid hormone may be used, a fragment of the human and bovine hormones at their amino terminus containing approximately the first 34 amino acids and commonly referred to as bovine parathyroid hormone 1-34 (bPTH 1-34and human parathyroid hormone 1-34 (hPTH 1-34) are preferred because of their biological potencies. Parathyroid hormone having fragments with more or less amino acids can be utilized, however parathyroid hormone having in the neighborhood of 80 to 85 amino acids is very expensive and may be no more effective as parathyroid hormone fragments having fewer amino acids. In general, any PTH fragments which have been shown to be effective when administered by injection should also be effective when encapsulated and administered orally in accordance with our invention.

The encapsulated parathyroid hormone or calcitonin is preferably administered orally as a buffered aqueous solution. Any pharmaceutically acceptable aqueous buffer may be utilized so long as it does not destroy the activity of the encapsulated polypeptide hormones and is suitable for oral administration. A preferred aqueous buffer is 20 mM NaCl containing 5 mM Tris-HCl which may have a pH of between 4.0 and 8.0.

Examples of practice are as follows:

Purified salmon and human calcitonin or human parathyroid hormone (1-34 amino acid fragment) were incorporated into liposomes consisting of natural or synthetic phospholipids and positively-charged amine-containing amphiphile. Liposomes containing the entrapped hormones were isolated by centrifugation, resuspended in buffer and administered by stomach tube to fasted normal rats (calcitonin) or fasted parathyroid-ectomized rats (parathyroid hormone). The serum calcium was determined at various time intervals in treated and untreated animals to assess the effect of the respective preparations.

EXAMPLE 1

450 micromoles of egg phosphatidylcholine (ePC) and 50 micromoles of stearylamine (SA) were dissolved in 2 to 3 ml of anhydrous chloroform placed in a 30 ml glass stopper tube and the solvent was removed in vacuo. To the thin film of lipid remaining on the wall of the tube was added 5.0 ml of buffer (20 mM NaCl containing 5 mM Tris, pH 7.4) containing 1 mg human PTH (hPTH 1-34) and $1\times10^6$ CPM of $I^{125}$-human PTH tracer (hPTH 1-34). The buffer was mixed at room temperature for 5 minutes using a vortex mixer.

After vortexing the mixture was sonicated for 3 minutes at room temperature using the cuphorn of a Heat Systems Ultrasonics sonicator at maximal output. The mixture was transferred to a polycarbonate tube and centrifuged at 4° C. using 50 Ti rotor and L265B ultracentrifuge (Beckmann Instruments) for 16 hours at 120,000 xg. The pellet, consisting of liposomes containing human PTH (1-34), was resuspended in 1.0 ml of of buffer (20 mM NaCl containing 5 mM Tris, pH 7.4) containing 2% cysteine as a preservative.

Oral administration of varying amounts of the egg phosphatidylcholine/stearylamine liposomes containing human PTH to parathyroidectomized rats had the effect on the serum calcium after 2 hours as shown in Table 1:

TABLE 1

| Dose | Changes in serum $Ca^{2+}$ mg/dl |
|---|---|
| None | −0.13 |
| 20 μg PTH | −0.03 |
| 30 μg PTH | +0.28 |
| 40 μg PTH | +0.92 |

The effect of oral free human PTH was compared to that of liposome-entrapped PTH (egg PC/stearylamine, 9/1) after 2 hr. The results are shown in Table 2.

TABLE 2

| Preparation | Change in Serum $Ca^{2+}$ mg/dl |
|---|---|
| Free PTH, 40 μg | +0.08 0.25[3] |
| Liposomal PTH, 40 μg | +0.37 0.02[3] |

[3] test run in triplicate, mean ± Std. error of mean

Other liposome preparations and other control studies were done with the results being shown in Table 3. The results show the effect on serum calcium 2 hours after oral administration to rats.

TABLE 3

| Preparation | Change in serum $Ca^{2+}$ mg/dl |
|---|---|
| Buffer alone | −0.10 |
| Buffer + 2% cysteine | −1.04 |
| ePC/SA (9/1)-empty liposome | −0.88 |
| Empty liposome + free PTH, 40 g | −0.6 |
| Free PTH, 40 μg | −0.05 |
| Buffer + 2% Cysteine | +0.27 ± 0.07[3] |
| ePC/SA (9/1) 40 μg PTH | +0.98 ± 0.24[3] |
| ePC/cholesterol/stearylamine (7/2/1) 40 μg PTH | +0.54 ± 0.24[3] |
| ePC/Cholesterol/dietylphosphate (7/2/1) 40 μg PTH | +0.56 ± 0.03[3] |
| ePC, 40 μg PTH | −0.07 |

[3] test run in triplicate, mean ± Std. error of mean

The above experiments demonstrates that orally administered ePC/stearylamine liposomes containing human PTH (hPTH 1-34) raise the serum calcium of rats while an equivalent dose of free PTH, buffer, PTH plus empty liposomes has no effect.

EXAMPLE 2

In this example, liposomes were prepared as in Example 1 except that the buffer contained 1 mg calcitonin (CT) instead of human PTH.

Liposomes consisting of egg phosphatidylcholine and stearylamine (8:2) and containing 28.4 units of salmon calcitonin (sCT) were administered by the oral route to fasted normal rats. Serum calcium was determined after 1 hour with the results being shown in Table 4.

TABLE 4

| Treatment | Change in Serum $Ca^{2+}$ mg/dl |
|---|---|
| None | 0 |
| Free sCT | 0 |
| Liposomal sCT (egg PC/SA, 8:2) | −1.0 |
| Lipo sCT + Aprotonin, 2000 i.u. | −2.2 |
| Lipo sCT + 40 mg sodium salicylate | −2.4 |
| Lipo sCT 39 mg salicylamide | −2.5 |
| Lipo sCT + 40 mg acetylsalicylate | −2.8 |
| Lipo sCT + 200 l methylsalicylate | −2.9 |

As is apparent from Table 4, oral administration of liposome encapulated calcitonin lowers serum calcium while the free hormone given in the same way has no effect. In addition, aspirin derivatives and aprotinin enhance the effect of liposomal CT. Suitable aspirin derivatives include sodium salicylate sodium salicylamide, acetylsalicylate and methylsalicylate. Aprotinin is an enzyme inhibitor marketed under the tradename Trasylol and identified in U.S. Pat. No. 2,890,986.

Additional control experiments were carried out to prove that liposomal entrapment is responsible for the oral effect of sCT. The results are shown in Table 5.

TABLE 5

| Treatment | Serum Ca, mg/dl | Change in Serum Ca, mg/dl |
|---|---|---|
| none | 9.2 | — |
| free sCT* | 8.9 | −0.3 |
| free sCT* + 20 mg aspirin | 8.4 | −0.8 |
| liposomal sCT** + 20 mg aspirin | 6.7 | −2.5 |

*sCT dose, 19.2U per rat by oral administration
**egg PC/stearylamine, 8/2

The results in Table 5 demonstrate that aspirin enhances slightly the effect of free CT. Maximal responses are seen with liposomal entrapment of sCT in ePC/stearylamine vesicles (8:2).

As is apparent, examples (1) and (2) demonstrate that calcitonin and parathyroid hormone can be entrapped in liposomes and then administered orally to achieve their biological effect. These preparations could be useful in the treatment of a large number of human diseases of calcium and skeletal metabolism. The particular dosages of PTH and calcitonin required to achieve desired serum calcium regulations will vary depending upon actual calcium level in each individual and the degree of disease or metabolic disorder.

Having thus described exemplary embodiments of the present invention, it should be noted by those skilled in the art that the within disclosures are exemplary only and that various other alternatives, adaptations and modifications may be made within the scope of the present invention. Accordingly, the present invention is not limited to the specific embodiments as illustrated herein, but is limited only by the following claims.

What is claimed is:

1. A method for regulating blood calcium levels in a mammal which comprises: orally administering to said mammal a blood calcium-regulating effective amount of a composition consisting essentially of an aqueous solution of a polypeptide hormone selected from the group consisting of parathyroid hormone and calcitonin, said polypeptide hormone being encapsulated in a liposome.

2. A method according to claim 1 wherein said polypeptide hormone is parathyroid hormone.

3. A method according to claim 2 wherein said polypeptide hormone is the hPTH 1–34 fragment of parathyroid hormone.

4. A method according to claim 1 wherein said polypeptide hormone is calcitonin.

5. A method according to claim 1 wherein said liposome contains from about 1 to 20 molar percentage of an alkylamine having the general formula $C_nH_{2n+1}NH_2$, where n is 12 to 20.

6. A method according to claim 5 wherein said alkylamine is stearylamine.

7. A method according to claim 1 including the additional step of administering salicylate, salicylamide, acetylsalicylate or methylsalicylate to said mammal to improve the blood calcium-regulating action of said polypeptide hormone encapsulated in said liposome.

8. A method according to claim 1 wherein said liposome is made from phospholipids selected from the group consisting of phosphatidylcholine, dimyristoylphosphatidylcholine and dipalmitoylphosphatidylcholine.

9. A composition for use in oral administration in mammals to regulate blood calcium levels, said composition consisting essentially of a polypeptide hormone selected from the group consisting of parathyroid hormone and calcitonin, said polypeptide hormone being encapsulated in a liposome, said liposome containing from about 1 to 20 molar percentage of an alkylamine having the general formula $C_nH_{2n+1}NH_2$, where n is 12 to 20.

10. A composition according to claim 9 wherein said polypeptide hormone is parathyroid hormone.

11. A composition according to claim 9 wherein said polypeptide hormone is calcitonin.

12. A composition according to claim 9 wherein said polypeptide hormone is the hPTH 1–34 amino acid fragment of parathyroid hormone.

13. A composition according to claim 9 wherein said alkylamine is stearylamine.

14. A composition according to claim 9 wherein said liposome is made from phospholipids selected from the group consisting of phosphatidylcholine, dimyristoylphosphatidylcholine and dipalmitoylphosphatidylcholine.

15. A method according to claim 1 including the additional step of administering aprotinin to said mammal to improve the blood calcium-regulating action of said polypeptide hormone encapsulated in said liposome.

16. A method according to claim 4 wherein said polypeptide hormone is salmon calcitonin.

17. A composition according to claim 11 wherein said polypeptide hormone is salmon calcitonin.

18. A composition for oral administration in mammals to regulate blood calcium levels, said composition comprising:
 a polypeptide hormone selected from the group consisting of parathyroid hormone and calcitonin, said polypeptide hormone being encapsulated in a liposome, said liposome containing from about 1 to 20 molar percentage of an alkylamine having a general formula $C_nH_{2n+1}NH_2$, where n is 12 to 20; and
 a pharmaceutically acceptable aqueous buffer solution have a pH of between about 4.0 and 8.0.

19. A composition for oral administration according to claim 18 wherein cysteine is added to said buffer solution as a preservative.

20. A composition for oral administration according to claim 18 wherein aprotinin, salicylate, salicylamide, acetylsalicylate or methylsalicylate is added to said buffer solution in an amount sufficient to improve the calcium-regulating action of said polypeptide hormone encapsulated in said liposome.

21. A composition for oral administration according to claim 18 wherein said polypeptide hormone is calcitonin.

22. A composition for oral administration according to claim 18 wherein said alkylamine is stearylamine.

* * * * *

UNITED STATES PATENT AND TRADEMARK OFFICE
CERTIFICATE OF CORRECTION

PATENT NO. : 4,692,433
DATED : September 8, 1987
INVENTOR(S) : Karl Y. Hostetler & Leonard J. Deftos It is certified that error appears in the above-identified patent and that said Letters Patent are hereby corrected as shown below:

Column 1, line 8, after "Services", insert -- and National Institute of Health Grant No. GM 24979 --.

Column 6, TABLE 4, change "Aprotonin" to -- Aprotinin -- and change "200 1" to -- 200 microliters --.

Signed and Sealed this

Sixth Day of December, 1988

*Attest:*

DONALD J. QUIGG

*Attesting Officer*     *Commissioner of Patents and Trademarks*